United States Patent
Medhekar et al.

(10) Patent No.: US 9,540,668 B2
(45) Date of Patent: Jan. 10, 2017

(54) REDUCED SUGAR SYRUPS AND METHODS OF MAKING REDUCED SUGAR SYRUPS

(71) Applicant: Tate and Lyle Ingredients Americas LLC, Hoffman Estates, IL (US)

(72) Inventors: Rohit Medhekar, Schaumburg, IL (US); Andrew Joseph Hoffman, West Point, IN (US)

(73) Assignees: Tate & Lyle Ingredients Americas LLC, Hoffman Estates, IL (US); Verenium Corporation, San Diego, CA (US)

( * ) Notice: Subject to any disclaimer, the term of this patent is extended or adjusted under 35 U.S.C. 154(b) by 0 days.

(21) Appl. No.: 13/752,453

(22) Filed: Jan. 29, 2013

(65) Prior Publication Data
US 2013/0197104 A1 Aug. 1, 2013

Related U.S. Application Data

(60) Provisional application No. 61/592,725, filed on Jan. 31, 2012.

(51) Int. Cl.
| C12P 19/14 | (2006.01) |
| A61K 47/26 | (2006.01) |
| C13K 1/06 | (2006.01) |
| A23L 2/60 | (2006.01) |
| A61K 8/60 | (2006.01) |
| A23L 27/30 | (2016.01) |
| A23L 1/236 | (2006.01) |

(52) U.S. Cl.
CPC ............. *C12P 19/14* (2013.01); *A23L 1/2363* (2013.01); *A23L 2/60* (2013.01); *A23L 27/30* (2016.08); *A23L 27/35* (2016.08); *A61K 8/60* (2013.01); *A61K 47/26* (2013.01); *C13K 1/06* (2013.01)

(58) Field of Classification Search
None
See application file for complete search history.

(56) References Cited

U.S. PATENT DOCUMENTS

| 3,654,082 | A | 4/1972 | Westmont, III |
| 4,182,756 | A | 1/1980 | Ramsay et al. |
| 4,445,938 | A | 5/1984 | Verwaerde et al. |
| 4,941,990 | A | 7/1990 | McLaughlin |
| 5,087,461 | A | 2/1992 | Levine et al. |
| 5,124,162 | A | 6/1992 | Bošković et al. |
| 5,266,467 | A | 11/1993 | Inglett |
| 7,273,740 | B2 * | 9/2007 | Callen et al. ............... 435/201 |
| 7,659,102 | B2 | 2/2010 | Callen et al. |
| 7,666,633 | B2 | 2/2010 | Callen et al. |

FOREIGN PATENT DOCUMENTS

| CN | 102626177 | | 8/2012 | |
| CN | 102676616 | | 9/2012 | |
| EP | 0252730 | * | 7/1987 | ............... C12N 9/28 |
| JP | S58-170492 | | 10/1983 | |
| JP | S64-016596 | | 1/1989 | |
| JP | H4-45794 | | 2/1992 | |
| JP | H5-38265 | | 2/1993 | |
| WO | WO-95/18776 | | 7/1995 | |
| WO | WO03075683 | * | 11/2003 | ............... A23L 1/105 |
| WO | WO 2005/000905 A1 | | 1/2005 | |
| WO | WO-2005/052148 | | 6/2005 | |
| WO | WO 2009/020741 A1 | | 2/2009 | |
| WO | WO 2009/094418 A2 | | 7/2009 | |
| WO | WO 2009/137839 A1 | | 11/2009 | |
| WO | WO2009137839 | * | 11/2009 | ............... C12P 19/12 |
| WO | WO-2010/118269 | | 10/2010 | |
| WO | WO 2010/132157 A2 | | 11/2010 | |
| WO | WO 2011/017093 A1 | | 2/2011 | |
| WO | WO 2011/049945 A2 | | 4/2011 | |
| WO | WO2010118269 | * | 4/2012 | ............... C12N 9/28 |

OTHER PUBLICATIONS

Annex to Form PCT/ISA/206, Issued for International Application No. PCT/US2013/023530, Dated Aug. 6, 2013.
International Search Report and Written Opinion for International Application Serial No. PCT/US2013/023530, Mailed Oct. 2, 2013.
Richardson et al., "A Novel, High Performance Enzyme for Starch Liquefaction", Journal of Biological Chemistry, vol. 277, No. 29, Jul. 19, 2002, pp. 26501-26507.
Atichokudomchai et al., "Reaction Pattern of a Novel Thermostable alpha-amylase", Elsevier, vol. 64, 2006, pp. 582-588.
Combined Search and Examination Report under Sections 17 and 18(3), Appl. No. GB1203703.2 report dated Jun. 29, 2012.
Fuelzyme®-LF, Thermostable, Low pH, Alpha-Amylase for Starch Liquefaction, Verenium the Nature of Energy. (2007 Copyright date).
Fuelzyme®-LF, Next-Generation, High Performance Alpha-Amylase for Starch Liquefaction, Verenium the Nature of Energy. (2007 Copyright date).

(Continued)

*Primary Examiner* — Paul Holland
(74) *Attorney, Agent, or Firm* — RatnerPrestia

(57) ABSTRACT

A reduced sugar syrup having an advantageously low viscosity is prepared by hydrolysis of starch or starchy material using a particular type of alpha amylase enzyme which yields a saccharide distribution having a low DP1-2 and low DP11+ content. The DP4 content of the syrup may be favorably increased by using a maltotetragenic alpha amylase enzyme in combination with the aforementioned alpha amylase enzyme. The syrup is useful in the production of food, beverage, animal feed, animal health and nutrition, pharmaceutical, and cosmetic compositions and may be combined with a high intensity sweetener to provide a composition capable of being substituted for conventional corn syrups.

13 Claims, 1 Drawing Sheet

(56) References Cited

OTHER PUBLICATIONS

Notification Concerning Transmittal of International Preliminary Report on Patentability (Chapter 1) of the Patent Cooperation Treaty) Issued on Aug. 5, 2014 for Application No. PCT/US2013/023530.
Chinese Office Action mailed Jan. 4, 2016 in Chinese Application No. 201380007429.7.
Richardson, T.H. et al., "Synthetic construct alpha-amylase precursor (BD5088) gene, complete cds," Accession No. AF504065, Jul. 15, 2002, GenBank.

* cited by examiner

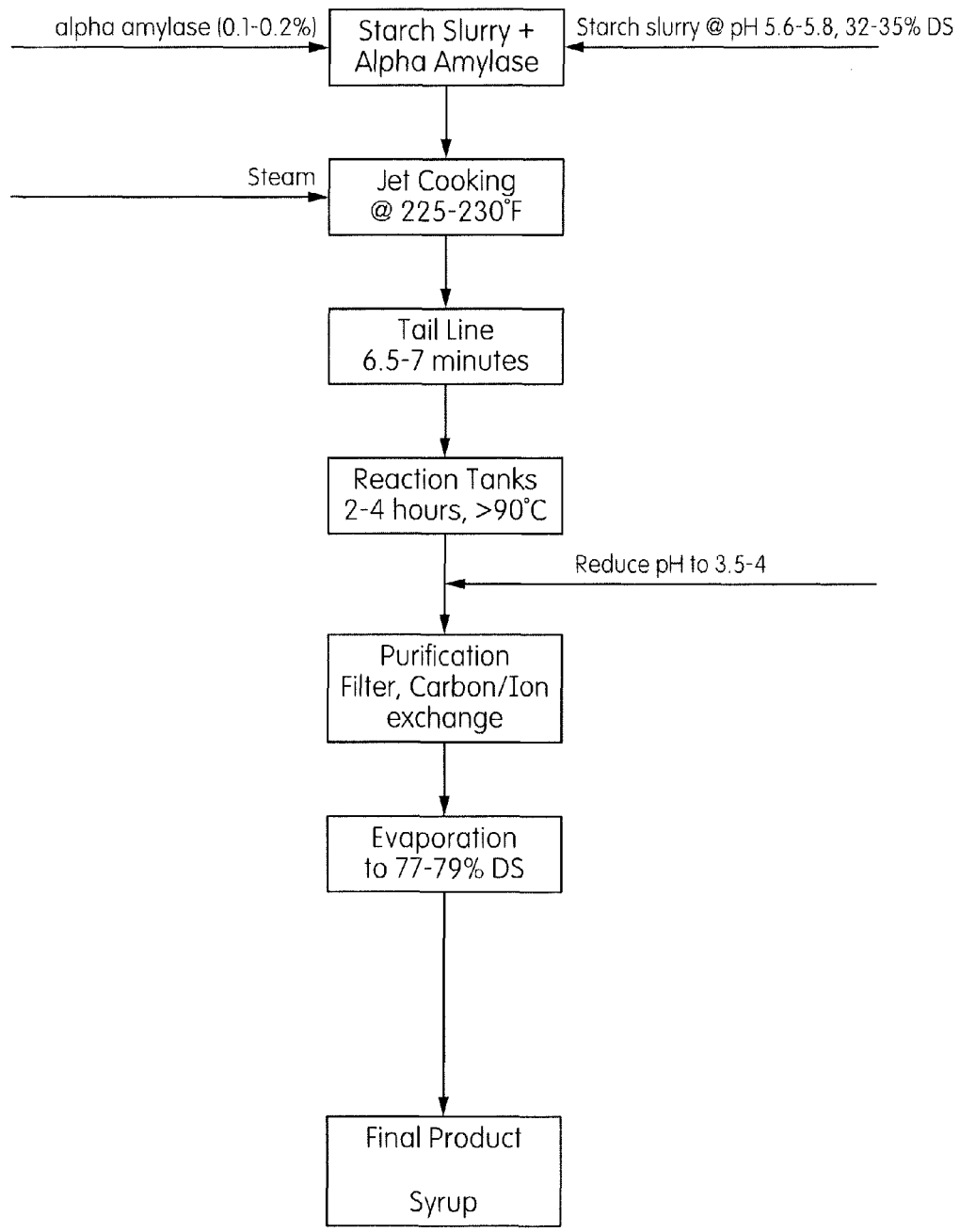

REDUCED SUGAR SYRUPS AND METHODS OF MAKING REDUCED SUGAR SYRUPS

CROSS-REFERENCE TO RELATED APPLICATION

This application claims priority to U.S. Provisional Application No. 61/592,725, filed Jan. 31, 2012, the disclosure of which is incorporated herein by reference in its entirety for all purposes.

FIELD OF THE INVENTION

The invention relates to syrups useful as food, beverage, animal feed, animal health and nutrition, and cosmetic ingredients which are relatively low in sugar content and viscosity, as well as methods for making such syrups.

BACKGROUND OF THE INVENTION

Consumer products with high sugar content have come under wide criticism for their purported links to obesity and associated health conditions. Consumers are increasingly looking for products that have low sugar content on their ingredients label. For label purposes, sugars are explicitly defined as mono or dimeric carbohydrates (DP1-2, where DP is "degree of polymerization"). To fulfill a low sugar content need, food companies are actively investigating ingredient formulations that will reduce the sugar content of their formulations. Current corn syrups on the market can have a sugar content as high as 95% (HFCS); typically, the sugar content ranges from 40% to 95%. A 63 dextrose equivalent (DE) corn syrup such as Sweetose® 4300 will have a sugar content of 64-66% and a high maltose syrup can have a sugar content in the range of 40-60%. These syrups are currently used as bulking agents, sweeteners, texture modifiers, and viscosity agents and for moisture control in food applications. For bulking syrups, viscosity is an important physical property. One method of reducing sugar content in corn syrups is to substitute the sugars with higher carbohydrate polymers (DP>11). But this could significantly change the colligative properties of these syrups, especially the viscosity. A change in viscosity cannot only adversely affect the aesthetic value of the food product but also creates a need for special manufacturing equipment. To avoid these issues, there is a need for a corn syrup that has substantially lower sugar content but possesses a viscosity similar to that of a 63 DE corn syrup.

Some companies are currently using polyols to reduce the sugar content of syrups. However, polyols can be expensive and many of them have undesired gastrointestinal side effects.

BRIEF SUMMARY OF THE INVENTION

The invention provides a method of making a reduced sugar, lower viscosity syrup, comprising contacting a starch or starchy material with a first alpha amylase enzyme in an aqueous medium for a time effective to hydrolyze the starch or starchy material to provide a reaction product having a saccharide distribution having a DP1+DP2 content of about 10% to about 25%, a DP3-11 content of about 70% to about 90%, and a DP11+ content of 0% to about 15%, wherein the first alpha amylase enzyme is a polypeptide encoded by a nucleic acid having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to GenBank Accession No. AF504065 (SEQ ID NO:1) or an amino acid sequence comprising an enzymatically active fragment of said polypeptide.

The above-mentioned method may comprise one or more of the following further steps: filtering the reaction product; contacting the reaction product with activated carbon; contacting the reaction product with an ion exchange resin; removing water from the reaction product to achieve a dry solids content of from about 65% to about 85%; subjecting the reaction product to ultrafiltration using a membrane; and/or combining the reaction product with at least one high intensity sweetener. In one embodiment, the method comprises the further steps of filtering the reaction product, contacting the reaction product with activated carbon and an ion exchange resin, and removing water from the reaction product to achieve a dry solids content of from about 65% to about 85%. In another embodiment, the method is conducted such that the starch or starchy material is not contacted with acid or any enzyme other than the first alpha amylase enzyme.

In one aspect of the above-mentioned method, the aqueous medium initially has a pH of from about 5 to about 7. The contacting step may, for example, be carried out at a temperature of from about 75° C. to about 120° C.

In one embodiment, the above-mentioned method may be conducted such that a slurry of the starch or starchy material, aqueous medium and first alpha amylase enzyme is initially heated, e.g., jet cooked, at a first temperature of from about 100° C. to about 115° C. and then maintained at a second temperature of from about 80° C. to about 95° C.

In one embodiment, an amount of the first alpha amylase enzyme is used in the above-mentioned method which is from about 0.01 to about 0.2 weight % of the amount of starch or starchy material.

The starch used in the method may be a corn starch. The starchy material may be from corn.

The DP11+ content of the reaction product obtained may, in one embodiment, be from 0-5%. The saccharides may have a DP4 content of at least about 35%. In one embodiment, the saccharides have a DP4 content of at least about 35% and a content of less than about 6% with respect to each of DP5 to DP10.

The reaction product obtained by the above-mentioned method may, in one embodiment, have a viscosity of less than about 1500 poise at 20° C. when the reaction product has a dry solids content of 80%.

The above-mentioned method may include a step wherein the starch or starchy material is additionally contacted with a maltotetragenic alpha amylase (i.e., contacted with a maltotetragenic alpha amylase as well as the first alpha amylase enzyme).

In one embodiment of the above-mentioned method, a slurry of the starch or starchy material, aqueous medium and first alpha amylase enzyme is initially jet cooked to provide a liquefied starch mixture and the liquefied starch mixture is subsequently contacted with a maltotetragenic alpha amylase. The first alpha amylase enzyme may be present in the liquefied starch mixture during the subsequent contacting with the maltotetragenic alpha amylase. The maltotetragenic alpha amylase may be a variant of a *Pseudomonas saccharophila* maltotetraohydrolyase. The maltotetragenic alpha amylase may be a variant of a wild-type maltotetraohydrolyase having the amino acid sequence of SEQ ID NO. 2 set forth in WO 2010/132157 (SEQ ID NO:2), comprising:

(i) a G223E amino acid substitution, and ii) up to 24 additional amino acid deletions, additions, insertions, or substitutions compared to the amino acid sequence of SEQ ID NO. 2 set forth in WO 2010/132157 (SEQ ID NO:2); or (iii) at least 70% sequence identity to the amino acid sequence of SEQ ID NO. 2 set forth in WO 2010/132157 (SEQ ID NO:2), wherein the variant has alpha-amylase activity.

In one aspect of the invention, the starch or starchy material is additionally contacted with a maltotetragenic alpha amylase, such as a variant of a *Pseudomonas saccharophilia* maltotetraohydrolyase (i.e., the starch or starchy material is contacted with a maltotetragenic alpha amylase as well as the first alpha amylase enzyme). A slurry of the starch or starchy material, aqueous medium and first alpha amylase enzyme may be initially jet cooked to provide a liquefied starch mixture and the liquefied starch mixture is subsequently contacted with the maltotetragenic alpha amylase. Using a combination of these different enzymes in this manner achieves hydrolysis of the starch or starchy material in a manner which helps to decrease or minimize the formation of sugars (DP1+2) and higher oligosaccharides (DP11+) while increasing or maximizing the content of DP4 in the resulting syrup.

In another aspect, the invention provides a method of making a reduced sugar, lower viscosity syrup, comprising:
(a) contacting a starch or a starchy material with a first alpha amylase enzyme in an aqueous medium, optionally under high shear conditions such as jet cooking, at a first temperature to provide a fluid mass of gelatinized starch;
(b) maintaining the fluid mass at a second temperature for a time effective to provide a reaction product having a saccharide distribution having a DP1+DP2 content of about 10% to about 25%, a DP3-11 content of about 70% to about 90%, and a DP11+ content of 0% to about 15%, wherein the first alpha amylase enzyme is a polypeptide encoded by a nucleic acid having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to GenBank Accession No. AF504065 (SEQ ID NO:1) or an amino acid sequence comprising an enzymatically active fragment of said polypeptide; and
(c) subjecting the reaction product to one or more purification or processing steps to provide the reduced sugar, lower viscosity syrup;
wherein the only type of enzyme used in the method is alpha amylase.

Step (a) may be carried out, for example, at a temperature of 90° C. or greater or 100° C. or greater, e.g., about 100° C. to about 115° C., about 104° C. to about 108° C., or about 107° C. to about 110° C. Step (a) may be carried out, for example, for a time of from about 2 to about 20 minutes. Step (b) may be carried out, for example, at a temperature of from about 80° C. to about 100° C., about 80° C. to about 95° C., or about 90° C. to about 95° C. or a temperature greater than 90° C. Step (b) may be carried out, for example, for a time of from about 1.5 to about 5 hours, about 2 to about 4 hours, or about 3 hours. The second temperature may be lower than the first temperature.

The invention also pertains to a syrup comprising water and saccharides, the saccharides having a saccharide distribution so as to provide a DP1+DP2 content of about 10% to about 25%, a DP3-11 content of about 70% to about 90%, and a DP11+ content of 0% to about 15%, wherein the syrup has a viscosity of not more than about 1400 poise at 20° C. when the syrup has a dry solids content of 80%. In one aspect, the saccharides have a saccharide distribution so as to provide a DP4 content of at least about 35% and a content of less than about 6% with respect to each of DP5 to DP10. In other aspects, the saccharides have a saccharide distribution so as to provide a DP11+ content of not more than 10% or not more than 5%.

Also afforded by the present invention is a food, beverage, animal feed, animal health and nutrition, pharmaceutical, or cosmetic product comprising the aforementioned syrup(s) and at least one food, beverage, animal feed, animal health and nutrition, pharmaceutical, or cosmetic ingredient.

Another aspect of the invention relates to a sweetener product comprising the syrup(s) and at least one high intensity sweetener.

In one embodiment, a syrup is provided comprising water and saccharides, the saccharides having a saccharide distribution of DP1 1-4%; DP2 10-15%; DP3 9-13%; DP4 7-11%; DP5 6-10%; DP6 13-19%; DP7 12-17%; DP8 4-7%; DP9 3-7%; DP10 2-6%; DP11 7-15%; DP11+ 0-4%, the total equaling 100%. A food, beverage, animal feed, animal health and nutrition, pharmaceutical, or cosmetic product comprising the aforementioned syrup and at least one food, beverage, animal feed, animal health and nutrition, pharmaceutical, or cosmetic ingredient is provided in another embodiment. Still another aspect provides a sweetener product comprising the aforementioned syrup and at least one high intensity sweetener.

Another embodiment of the invention provides a method of making a reduced sugar, lower viscosity syrup for food, beverage, animal feed, animal health and nutrition, pharmaceutical, and cosmetic compositions, comprising:
(a) jet cooking a slurry of a starch or a starchy material, a first alpha amylase enzyme and an aqueous medium at a first temperature of from 100° C. to 115° C.;
(b) maintaining the slurry at a second temperature of from 80° C. to 95° C. for a time effective to provide a reaction product having a saccharide distribution having a DP1+DP2 content of 10% to 25%, a DP3-11 content of 70% to 90%, and a DP11+ content of 0% to 15%, wherein the first alpha amylase enzyme is a polypeptide encoded by a nucleic acid having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to GenBank Accession No. AF504065 (SEQ ID NO:1) or an amino acid sequence comprising an enzymatically active fragment of said polypeptide; and
(c) subjecting the reaction product to one or more purification or processing steps to provide the reduced sugar, lower viscosity syrup;
wherein the only type of enzyme used in the method is alpha amylase.

DESCRIPTION OF THE DRAWING

FIG. 1 illustrates in schematic form an exemplary embodiment of the process of the invention.

DETAILED DESCRIPTION OF THE INVENTION

The term, "DPN", as used herein, refers to the degree of polymerization, where N is the number of monomeric units (i.e., glucose or dextrose units) in the saccharide, thus DPN reflects the composition of the saccharide. For example, DP1 is a monosaccharide; DP2 is a disaccharide; DP1+2 is the total of mono- and di-saccharides; DP3-11 is the total of DP 3 to DP11; and DP11+ is the total of saccharides containing more than 11 monomeric units per molecule. DPN is expressed as a weight percent of an individual saccharide on a total saccharide dry weight basis. The DPN composition of a product was determined using high performance liquid chromatography (HPLC). Samples were diluted to approximately 5% solids with Milli-Q water and filtered through a 0.45 μm filter. Twenty microliters of sample was injected. The separation was accomplished using a Bio-Rad HPX 42A column, a styrene divinyl benzene resin based column in the silver form coupled with a refractive index detector. The 42A column is more lightly cross-linked than the columns used to analyze HFCS. The lower cross linking gives the resin an open structure, making it more permeable to higher molecular weight structures. That coupled with the ligand-ligand reaction between the silver counter ion on the resin and the hydroxyl groups on the sugars allows separation up to DP12 with a run time of less than 20 minutes. Quantitation is done using area percent with no response factors since there are few commercially available pure sugar standards above maltopentose. The refractive index responses for all these sugars is expected to be very similar.

The term, "DS", as used herein, refers to the percent dry solids of a substance as determined using the computer program, Refractive Index Dry Substance (RI-DS), Standard Analytical Method E-54, Corn Refiners Association, 6$^{th}$ Edition, 1977, E-54, pp. 1-11.

The term "sugar", as used herein, refers to mono- and/or di-saccharides.

The term, "syrup", as used herein, refers to aqueous solutions of saccharides.

The term, "viscosity", as used herein, refers to the resistance of a fluid to flow. The viscosity of a syrup is typically affected by temperature and solids concentration. Viscosity is expressed in terms of poise (P) or centipoise (cps) at a given temperature and a given % DS.

The syrup preparation method of the present invention utilizes starch or starchy material as a feedstock or starting material. Starch or starchy material can be obtained from a number of different sources using any number of methods routinely practiced in the art. For example, starch or starchy material can be obtained from corn (for example, dent corn) or another cereal feedstock such as rice, wheat, barley, oats, or sorghum through well-known wet-milling and dry-milling techniques. In wet milling, corn or other feedstock can be steeped for a period of time and then ground to separate the germ, which contains the oil, from the other components. The remaining non-germ material is a slurry that includes starch, protein (e.g., gluten) and fiber, which can be separated into different streams. Starch steams also can be obtained from corn or another starch-rich feedstocks through dry milling techniques, which also are practiced routinely in the art. In addition, starch streams can be obtained from a root or tuber feedstock such as potato or cassava using either wet-milling or dry-milling processes.

An advantage of one embodiment of the present invention is that a starch or starchy material may be directly converted into a product having a desirable saccharide distribution and viscosity, as described previously herein, using a single particular type of enzyme. That is, in one embodiment of the invention the only type of enzyme used in the method of making the reduced sugar, lower viscosity syrup is alpha amylase (although, as will be explained subsequently in more detail, two different alpha amylase enzymes may be utilized in one embodiment of the present invention). This contrasts with methods previously known in the art for making reduced sugar, low viscosity syrups wherein two steps are required (e.g., a first liquefaction step using an acid or a first type of enzyme, followed by a second hydrolysis step using a second type of enzyme).

Conventionally, an alpha-amylase is used in processes for making fermentable sugars from starch, whereby the starch is treated with the alpha-amylase to make a liquefact, which is then subsequently reacted with a second enzyme, a glucoamylase, to convert the intermediate liquefact to fermentable sugars (for example, glucose), see for example U.S. Pat. Nos. 7,273,740, 7,666,633, and 7,659,102. In contrast, another advantage of the present invention is the novel and unexpected finding that under appropriate conditions the liquefact that can be generated using an alpha-amylase having at least 70%, 75%, 80%, 85%, 90%, 95%, or more, or complete (100%) sequence identity to GenBank Accession No. AF504065 (SEQ ID NO:1) or an amino acid sequence comprising an enzymatically active fragment thereof, can be utilized directly for the production of the reduced sugar, low viscosity syrups of the present invention. The ability to use a single enzyme to convert a starch or starchy material to a syrup of the type described herein simplifies the manufacturing process, thereby reducing costs.

The first alpha amylase enzyme employed in the present invention is a polypeptide encoded by a nucleic acid having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to GenBank Accession No. AF504065 (SEQ ID NO:1) or an amino acid sequence comprising an enzymatically active fragment of said polypeptide. Alpha amylase enzymes suitable for such use in the present invention are known in the art and are described, for example, in U.S. Pat. Nos. 7,273,740, 7,666,633, and 7,659,102, each of which is incorporated herein by reference in its entirety for all purposes. Such alpha amylases can produce liquefaction products that have a unimodal molecular weight profile of saccharides centered within the molecular weight range of 1000 to 2000. Sequence ID No. 1 in the aforementioned patents describes a nucleic acid which encodes a polypeptide useful for practicing the present invention. The polypeptide used as the first alpha amylase enzyme in the present invention thus may be a polypeptide encoded by a nucleic acid having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to Sequence ID No. 1 as set forth in U.S. Pat. Nos. 7,273,740, 7,666,633, and 7,659,102 (SEQ ID NO:1), or an enzymatically active fragment thereof. Sequence ID No. 2 in the aforementioned patents (SEQ ID NO:3) describes an amino acid sequence which may be present in a polypeptide useful for practicing the present invention. Thus, a polypeptide which may be used as the first alpha amylase enzyme in the invention may comprise an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to Sequence ID No. 2 as set forth in U.S. Pat. Nos. 7,273,740, 7,666,633, and 7,659, 102 (SEQ ID NO:3), or an enzymatically active fragment thereof. If so desired, the first alpha amylase enzyme may be immobilized on a suitable support or within a suitable matrix.

The amount of first alpha amylase enzyme utilized in the process of the present invention may be varied and selected depending upon the desired rate of reaction, reaction conditions and so forth, but generally will be within the range of from about 0.01 to about 0.2% or from about 0.1 to about 0.2% based on the dry weight of the starch or starchy material being reacted.

The starch or starchy material may be combined with water to form a slurry, typically containing from about 25 weight % to about 40 weight % (e.g., about 32 to about 35 weight %) starch or starchy material. The pH of the aqueous medium may be adjusted as desired by the addition of one or more acids or bases. Typically, it will be desirable for the pH of the aqueous medium to be somewhat (i.e., weakly) acidic to neutral, e.g., within the range of from about 4 to about 7 (in one embodiment, from about 5.5 to about 6).

The process of the present invention may be carried out using at least two heating stages, wherein in a first heating stage the aqueous slurry of starch or starchy material and first alpha enzyme is heated at a relatively high temperature (e.g., 100° C. or greater) for a relatively short period of time and subsequently in a second heating stage the aqueous slurry is heated at a lower temperature than in the first heating stage (e.g., 80° C. to 95° C.) for a longer period of time than in the first heating stage. It will often be advantageous to carry out the first heating stage under conditions effective to gelatinize or at least partially solubilize the starch. For example, after combining with the first alpha amylase enzyme, the slurry may be first subjected to a high shear cooking step wherein high shear is applied to the starch while the slurry is heated to a relatively high temperature (e.g., about 90° C. or more or about 95° C. or more or about 100° C. or more or about 105° C. or more, but typically not greater than about 115° C.) for a comparatively short period of time (e.g., about 2 to about 20 minutes). The high shear cooking step may be carried under pressure, i.e., at a pressure greater than atmospheric pressure. For example, a pressure of at least about 5 kg/cm$^2$ (e.g., about 8 to about 11 kg/cm$^2$) may be utilized. Generally, such high shear conditions are selected to be effective to gelatinize (at least partially solubilize) the starch. Jet cooking techniques may be used, wherein the slurry is mixed with steam at high temperature and pressure (i.e., superatmospheric pressure) while passing through a narrow orifice. The amount of steam may be controlled such that complete steam condensation is achieved or, alternatively, the amount of steam may be in excess. The steam pressure may be from about 5 bar to about 8 bar (absolute), for example. The intense turbulence resulting from the near-instantaneous heating of the starch and the passage of steam through the jet cooker promotes the rupture and dissolution of starch granules. The viscosity of the slurry is lowered due to the mechanical shearing of the high molecular weight starch chains. The starch slurry may thereby be gelatinized and thinned.

For example, the slurry may be pumped through a steam jet having a narrow orifice in a jet cooking step to quickly raise the temperature to between about 100° C. and about 115° C. (e.g., from about 104° C. to about 108° C. or from about 107° C. to about 110° C.). The starch is immediately gelatinized and, due to the presence of the first alpha amylase, partially depolymerized through random hydrolysis of glycosidic bonds by the enzyme to a fluid mass which is easily pumped. In one embodiment, the starch slurry, after being passed through the steam jet, may be resident in a tail line for a period of time of from about 5 to about 8 minutes. The fluid mass may then be transferred to a vessel, such as a stirred tank, wherein reaction of the starch with the first alpha amylase enzyme may be continued at a second, somewhat lower temperature (e.g., about 80-95° C.) until the desired saccharide distribution is achieved. In one embodiment of the invention, the temperature of the fluid mass is maintained above 90° C. during the second heating step in order to inhibit the growth of microorganisms. Typically, the pH of the fluid mass is not adjusted or changed before proceeding with the second heating step. In such second heating step, high shear conditions and above-atmospheric pressures typically are not utilized. For example, the fluid mass may be stirred or otherwise mixed or agitated under low shear conditions and atmospheric (ambient) pressure. Generally speaking, increased reaction times will result in a higher degree of depolymerization, providing a lower content of DP11+ saccharides and thereby reducing the viscosity of the resulting syrup. The alpha amylase treatment thus may be carried out for an amount of time effective to provide a DP11+ content of, in various embodiments of the invention, not greater than 15%, not greater than 10%, not greater than 5%, not greater than 4%, not greater than 3%, not greater than 2%, not greater than 1%, or approximately 0%. However, it will also generally be desirable to halt the depolymerization before the mono- and di-saccharide content becomes unacceptably high. For example, the enzyme hydrolysis reaction may be stopped when the DP1+2 content reaches 10%, 11%, 12%, 13%, 14%, 15%, 16%, 17%. 18%, 19%, 20%, 21%, 22%, 23%, 24%, or 25%. The reaction time in the second heating step will typically be about 1.5 to about 5 hours or about 2 to about 4 hours or about 3 hours.

According to one embodiment of the invention, the aforementioned first alpha amylase enzyme is the only enzyme contacted with the starch (or starchy material) and the liquefaction product obtained by jet cooking of the starch (or starchy material). However, in another embodiment the starch (or starchy material) and/or liquefaction product is additionally contacted with at least one other enzyme. In particular, the liquefaction product containing the first alpha amylase enzyme may combined with a different alpha amylase enzyme such as a maltotetragenic alpha amylase and then further reacted until a syrup with the desired saccharide distribution is achieved. Accordingly, a slurry of the starch (or starchy material), aqueous medium and first alpha amylase enzyme is initially subjected to high shear, high temperature conditions (e.g., jet cooked) to provide a liquefied starch mixture and the liquefied starch mixture is subsequently contacted with a maltotetragenic alpha amylase. The first alpha amylase enzyme may be present in the liquefied starch mixture during the subsequent contacting with the maltotetragenic alpha amylase. If the maltotetragenic alpha amylase enzyme is not sufficiently robust to withstand the high temperatures experienced during jet cooking, it will be desirable to delay combining such enzyme with the starch until the liquefaction step is completed and the temperature of the liquefaction product has been lowered to a temperature (e.g., less than about 80° C.) where the activity of the maltotetragenic alpha amylase remains high over time (i.e., it is not inactivated significantly by the heat which is experienced).

In the aforementioned embodiment, the maltotetragenic alpha amylase may be any alpha amylase that selectively or preferentially produces a high proportion of DP4 oligosaccharide from the liquefied starch. Such maltotetragenic alpha amylases are well known in the art and include, for example, a wild-type *Pseudomonas saccharophila* maltotetraohydrolyase or a variant thereof. The maltotetraohydrolyase expressed by *Pseudomonas saccharophila* is variously referred to in the art as Amy3A, PSA, SAS, or PS4. Wild-type *Pseudomonas saccharophila* maltotetraohydrolyase may be encoded by a nucleotide sequence as set forth Zhou et al., "Nucleotide sequence of the maltotetraohydrolase gene from *Pseudomonas saccharophila*," FEBS Lett. 255: 37-41 (1989), incorporated herein by reference in its entirety. This nucleotide sequence has been assigned GenBank Accession No. X16732. The maltotetragenic alpha amylase may be a variant of a wild-type maltotetraohydrolyase having the amino acid sequence of SEQ ID NO. 2 set forth in WO 2010/132157 (SEQ ID NO:2), comprising:

(i) a G223E amino acid substitution, and (ii) up to 10, 11, 12, 13, 14, 15, 16, 17, 18, 19, 20, 21, 22, 23 or 24 additional amino acid deletions, additions, insertions, or substitutions compared to the amino acid sequence of SEQ ID NO. 2 set forth in WO 2010/132157 (SEQ ID NO:2); or (iii) at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to the amino acid sequence of SEQ ID NO. 2 set forth in WO 2010/132157 (SEQ ID NO:2), wherein the variant has alpha-amylase activity. Such variant maltotetragenic alpha amylases are described in WO 2010/118269 and WO 2010/132157, each of which is incorporated herein by reference in its entirety for all purposes. Suitable maltotetragenic alpha amylases are available from commercial sources, such as certain of the enzymes sold under the Grindamyl® PowerFresh brand name by Danisco (Genencor), e.g., Grindamyl® PowerFresh 3001. The maltotetragenic alpha amylase may be immobilized on a suitable support or within a suitable matrix, if so desired.

When a maltotetragenic alpha enzyme is additionally contacted with the liquefied starch mixture obtained from an initial jet cooking of starch or starchy material, the pH of the mixture may typically be maintained within the range of from about 4.5 to about 7. The temperature during such contacting may, for example, be from about 50 to about 70° C.

In one embodiment of the invention, the reaction product and syrup obtained have the following saccharide distribution: DP1 1-4%; DP2 10-15%; DP3 9-13%; DP4 7-11%; DP5 6-10%; DP6 13-19%; DP7 12-17%; DP8 4-7%; DP9 3-7%; DP10 2-6%; DP11 7-15%; DP11+ 0-4%, the total equaling 100%.

In another embodiment of the invention, the reaction product and syrup obtained have the following saccharide distribution: DP1 2-6%; DP2 12-16%; DP3 12-16%; DP4 38-46%; DP5-DP10 1-6% each; DP11 2-10%; DP11+ 0-2%.

The polydispersity ($M_w/M_n$) of the saccharides present in the reaction product and syrup is typically relatively low, e.g., not more than about 2 or not more than about 1.8 or not more than about 1.6.

The saccharide distribution may be monitored on a periodic basis using methods known in the art and further hydrolysis stopped by inactivating the enzyme by, for example, adding an amount of acid effective to lower the pH of the aqueous medium to a level where the enzyme is no longer active (e.g., a pH of from about 3 to about 4).

The reaction product thereby obtained may be subjected to one or more further purification or processing steps to provide a syrup suitable for use as a food, beverage, animal feed, or animal health and nutrition ingredient. For example, the reaction product may be filtered through a filter medium such as diatomaceous earth or the like to remove any insoluble substances and/or contacted with a decolorizing agent such as an ion exchange resin or activated carbon (typically, by passing the reaction product through a bed or column packed with the decolorizing agent). Depending upon the intended end use application, the pH of the product may be adjusted by addition of acid or base or treatment with an ion exchange resin. Ultrafiltration using a membrane or the like may be employed to further reduce the content of mono- and di-saccharides, if so desired. Water may be removed from the reaction product by distillation or other evaporative methods to provide the final syrup having the desired dry solids content and viscosity. Typically, the dry solids content of the syrup is advantageously between about 60 weight % and about 85 weight %. Generally speaking, it will be advantageous to include an amount of water effective to render the syrup clear and liquid at room temperature (20-25° C.). In one embodiment of the invention, the syrup may be dried to provide a solid product (e.g., in the form of a powder).

FIG. 1 is a schematic illustration of one embodiment of the present invention, wherein a slurry of starch is converted using a single alpha amylase enzyme to a reduced sugar, lower viscosity syrup by a process involving jet cooking of the starch slurry in the presence of the alpha amylase followed by continued reaction at a lower temperature. After deactivation of the enzyme by acidification, the reaction product is filtered and subjected to carbon treatment and/or ion exchange prior to being concentrated by evaporation to provide the final syrup having the desired dry solids content.

In certain embodiments of the invention, the syrup may exhibit the following viscosity profile:

70% DS: about 12 to about 22 poise at 20° C., about 5 to about 10 poise at 30° C.;

75% DS: about 80 to about 110 poise at 20° C., about 30 to about 40 poise at 30° C.;

80% DS: about 1000 to about 1500 poise at 20° C., about 250 to about 400 poise at 30° C.;

82% DS: about 4000 to about 8000 poise at 20° C., about 1000 to about 1600 poise at 30° C.

If so desired, the syrup of the present invention may be converted into dry form by complete or substantially complete removal of water by any suitable means such as spray-drying.

The sweetness of the syrup may be increased if so desired by combining the syrup with one or more high intensity sweeteners of either natural or synthetic origin. Natural high intensity sweeteners include, for example, mogrosides and steviol glycosides (stevia). Illustrative synthetic high intensity sweeteners include sucralose, saccharin, cyclamate, acesulfame potassium, neotame, aspartame, and the like. In one embodiment of the invention, an amount of high intensity sweetener is combined with the syrup to impart a perceived level of sweetness comparable to that of a conventional corn syrup having a relatively high content of mono- and di-saccharides.

As a result of the low content of polysaccharides (DP11+), the syrups of the present invention have advantageously low viscosities at a given dry solids content. This means that the syrup may be supplied in relatively concentrated form (i.e., a high DS content) while still having good flow properties, thus facilitating the incorporation of the syrup into various foodstuffs. A further advantage of a high DS (low water) content syrup of the present invention is that it will exhibit improved microbial stability as compared to a conventional reduced sugar starch hydrolyzate syrup of comparable viscosity and DP1+2 content, which necessarily must contain more water due to its higher levels of DP11+ polysaccharides.

The syrup of the present invention can be utilized in food, beverage, animal feed, animal health and nutrition, pharmaceutical, and cosmetic products to decrease the sugar content of such products with minimal impact on the physical properties of such products; and at the same time with minimal impact on the processes and equipment used for the manufacturing of such products due in part to the easier handling of such syrup. The syrup may be used in foods and feeds to soften texture, add volume, thicken, prevent crystallization of sugar, and/or enhance flavor.

In particular, the syrup is useful as a bulking agent that is low in sugar. It is capable of having an appearance, viscosity, crystallinity, mouthfeel, humectancy and other colligative properties similar to those of conventional, higher sugar corn syrups. As such, the syrups of the present invention can be readily substituted on an approximately equal weight or volume basis for conventional corn syrups in food, beverage, animal feed, animal health and nutrition, pharmaceutical, cosmetic products and the like, yet will effectively reduce the amount of sugar in such products. The syrups thus can be utilized to lower the sugar content of products without significantly altering the physical and sensory attributes of the products. One advantage of the syrups of the present invention is that they have improved (faster) drying rates as compared to conventional syrups containing a relatively high proportion of polysaccharides (e.g., saccharides having a DP of greater than 11).

The syrup afforded by the present invention is suitable for use in food, beverage, animal feed, animal health and nutrition, pharmaceutical, and cosmetic compositions, especially those which are reduced sugar or low sugar products. Non-limiting examples include its use as bulking, binding and coating ingredients; carriers for coloring agents, flavors/fragrances, and high intensity sweeteners; spray drying adjuncts; bulking, bodying and dispersing agents; and ingredients promoting moisture retention (humectants). Illustrative examples of products which can be prepared using the syrups described herein include beverages, baked goods, confectioneries, frozen dairy products, meats, breakfast cereals, dairy products, condiments, snack bars, soups, dressings, mixes, prepared foods, baby foods, diet preparations, peanut butter, syrups, sweeteners, food coatings, pet food, animal feed, animal health and nutrition products, dried fruit, sauces, gravies, jams/jellies, and the like.

The syrup of the present invention may, for example, be utilized to provide a moisture barrier in various foods. The syrup, optionally in admixture with one or more additional food ingredients, may be applied as a coating or layer on a food product which, once dried, helps to retard the transmission of water into or out of the food product. For instance, a sweet topping such as a glaze or frosting comprising the syrup may be formed on a surface of a baked good such as a doughnut, snack bar, cookie, a dry cereal (in the form of flakes, biscuits, or clusters, for example) or the like. The dried sweet topping acts as a moisture barrier, whereby the resulting food product has improved shelf life and exhibits a reduced tendency for the outer surface of the sweet topping to become sticky (tacky) over time. The dried sweet topping can also hinder the penetration of external moisture into the food product, thereby permitting the food product to maintain a desired level of crispness or crunchiness over a prolonged period of time when immersed in an aqueous environment. In another embodiment, a layer comprised of the syrup is present within a food product, such that it is interposed between two other layers (one of which contains moisture, with the other being lower in moisture content). The syrup-containing layer helps to slow down or prevent the migration of moisture from the one layer to the lower moisture content layer. This serves to maintain the crispiness/crunchiness of the lower moisture content layer as the food product is stored.

EXAMPLES

Example 1

15 kg of starch slurry (35% DS dent starch) was adjusted to pH 5.8 using 4M NaOH. 5.25 g of Veretase® enzyme (Verenium Corporation) (0.1% w/w starch dsb) was added to the slurry. The slurry was jet cooked at 107° C. with a 6-7 min residence time in the tail pipe. The jetted starch was collected and allowed to stir in a round bottom flask maintained at 85-90° C. Samples were collected for saccharide distribution analysis over time. The reaction was carried out for 3 hours and then killed by reducing the pH to 3 and cooling the syrup. The syrup was then filtered through Celite® filter aid and passed through activated carbon and ion exchange resin for purification. The syrup was then evaporated to 80% DS.

Table 1A shows the saccharide distribution of the reaction samples taken at different time intervals. Table 1B provides the molecular weight and polydispersity data for each sample.

TABLE 1A

| Time, min | DP1 | DP2 | DP3 | DP4 | DP5 | DP6 | DP7 | DP8 | DP9 | DP10 | DP11 | DP12 | DP13+ |
|---|---|---|---|---|---|---|---|---|---|---|---|---|---|
| 0 | 0.35 | 3.06 | 3.6 | 2.58 | 2.16 | 4.18 | 6.88 | 5.36 | 5.59 | 4.62 | | | 61.56 |
| 30 | 0.81 | 6.4 | 6.8 | 5.23 | 4.46 | 8.55 | 12.56 | 8.12 | 6.43 | 5.42 | | | 35.17 |
| 60 | 1.4 | 8.94 | 8.73 | 6.84 | 5.97 | 11.62 | 15.39 | 8.14 | 6.03 | 4.63 | 4.43 | 17.78 | |
| 90 | 1.69 | 10.3 | 9.57 | 7.6 | 6.74 | 13.37 | 16.13 | 7.44 | 5.78 | 4.62 | 3.7 | 13.01 | |
| 120 | 1.94 | 11.27 | 10.08 | 8.1 | 7.27 | 14.33 | 16.43 | 6.77 | 5.42 | 3.9 | 14.44 | | |
| 150 | 2.09 | 11.99 | 10.41 | 8.5 | 7.62 | 15.22 | 16.23 | 6.23 | 5.17 | 4.04 | 12.39 | | |
| 180 | 2.3 | 12.64 | 10.73 | 8.79 | 8.03 | 15.8 | 15.92 | 5.93 | 5.11 | 3.81 | 10.82 | | |
| Before GAC IX | 3.36 | 14.4 | 11.81 | 9.88 | 9.02 | 18.04 | 13.49 | 5.18 | 4.38 | 2.82 | 7.50 | 0.00 | 0.00 |
| After GAC IX | 2.81 | 13.7 | 11.49 | 9.75 | 8.96 | 17.83 | 13.55 | 5.45 | 4.67 | 3.21 | 8.51 | 0.00 | 0.00 |

TABLE 1B

| Time, min | $M_n$ | $M_w$ | MP | $M_z$ | Polydispersity |
|---|---|---|---|---|---|
| 0 | 1139 | 2025 | 1500 | 3342 | 1.78 |
| 30 | 907 | 1503 | 1334 | 2201 | 1.66 |
| 60 | 807 | 1299 | 1207 | 1840 | 1.61 |
| 90 | 747 | 1198 | 1120 | 1701 | 1.60 |
| 120 | 712 | 1145 | 1045 | 1679 | 1.61 |
| 150 | 681 | 1081 | 1018 | 1540 | 1.59 |
| 180 | 650 | 1030 | 994 | 1452 | 1.59 |
| Final | 684 | 1049 | 1067 | 1425 | 1.53 |
| Final | 648 | 1016 | 1010 | 1403 | 1.57 |

The viscosity profile of the syrup thereby obtained at 71% DS was as shown in Table 2 (compared to SWEETOSE® 4300 63 DE conventional corn syrup, 71% DS).

TABLE 2

| | Temp., ° C. | | | | | | |
|---|---|---|---|---|---|---|---|
| | 20 | 30 | 40 | 50 | 60 | 70 | 80 |
| Syrup of the Invention, | 752 | 358 | 190 | 111 | 71 | 51 | 36 |

TABLE 2-continued

| | Temp., ° C. | | | | | | |
|---|---|---|---|---|---|---|---|
| | 20 | 30 | 40 | 50 | 60 | 70 | 80 |
| viscosity in cps | | | | | | | |
| SWEETOSE® 4300, viscosity in cps | 586 | 273 | 142 | 81 | 50 | 33 | 24 |

Example 2

15 kg of starch slurry (35% DS dent starch) was adjusted to pH 5.3 using 4M NaOH. 5.25 g of Veretase® enzyme (0.1% w/w starch dsb) was added to the slurry. The slurry was jet cooked at 107° C. with a 6-7 min residence time in the tail pipe. The jetted starch was collected and allowed to stir in a round bottom flask maintained at 85-90° C. Samples were collected for saccharide distribution analysis over time. The reaction was carried out for 3 hours and then killed by reducing the pH to 3 and cooling the syrup. The syrup was then filtered through Celite and passed through activated carbon and ion exchange resin for purification. The syrup was then evaporated to 80% DS.

Table 3 shows the saccharide distribution of the reaction samples taken at various times.

TABLE 3

| Time, (min) | Dextrose | DP2 | DP3 | DP4 | DP5 | DP6 | DP7 | DP8 | DP9 | DP10 | DP11 | DP12 | DP13+ |
|---|---|---|---|---|---|---|---|---|---|---|---|---|---|
| 0 | 0.56 | 3.76 | 4.27 | 3.2 | 2.72 | 5.17 | 7.98 | 6.05 | 5.52 | | 5.21 | | 55.7 |
| 30 | 0.98 | 6.43 | 6.81 | 5.28 | 4.59 | 8.8 | 12.23 | 8.09 | 6.47 | 5.2 | 4.38 | | 30.7 |
| 60 | 1.28 | 8.24 | 8.23 | 6.48 | 5.7 | 10.97 | 14.66 | 7.99 | 6.23 | 5.09 | | 4.48 | 20.52 |
| 90 | 1.51 | 9.47 | 9.05 | 7.2 | 6.33 | 12.5 | 15.8 | 7.5 | 5.89 | 4.95 | 3.61 | 16.18 | |
| 120 | 1.7 | 10.57 | 9.68 | 7.78 | 7.04 | 13.78 | 16.15 | 7.08 | 5.53 | 4.77 | 3.46 | 12.53 | |
| 150 | 2.03 | 11.43 | 10.18 | 8.23 | 7.54 | 14.64 | 16.13 | 6.7 | 5.41 | 4.26 | 2.97 | 10.48 | |
| 180 kill (pH3) | 2.26 | 12.25 | 10.57 | 8.65 | 7.9 | 15.47 | 15.84 | 6.33 | 5.13 | 4.15 | 3.05 | 8.4 | |

Example 3

Dent starch (5.25 kg) was mixed with 9.75 kg water to make a 35% DS starch slurry. The pH of the slurry was adjusted to 5.9 using 10% NaOH. 5.25 g of Veretase® enzyme was added to the slurry. The slurry was then jet cooked at 107° C. at a rate of 350 mL/min, which provides a residence time in the tail of 6-7 minutes. The liquefact was collected and cooled to 65° C. in a water bath. After cooling, 10.5 g of Grindamyl® PowerFresh 3001 enzyme (Danisco) was added to the syrup. Samples of the reaction mixture were collected at different time intervals. After 3 hours, the reaction was stopped by reducing the pH to 4. Table 4 shows the saccharide distribution of the reaction samples taken at different times. The time "t=0" is the time at which jetting (liquefaction) had been completed and the Grindamyl® enzyme was added.

By way of comparison, when a typical liquefact prepared by jet cooking a starch slurry using a conventional heat-stable alpha amylase (e.g., those that produce a bimodal product distribution) is reacted with Grindamyl® PowerFresh 3001 enzyme, the reaction product (syrup) obtained has a relatively high content of DP4 saccharide (e.g., somewhat in excess of 40%). However, the product also contains a large proportion of higher oligosaccharides (e.g., about 30% or more DP11+), which adversely affects the viscosity of the syrup. The higher oligosaccharides apparently are not effectively hydrolyzed to lower saccharides by either the Grindamyl® PowerFresh enzyme or the conventional alpha amylase enzyme. The higher oligosaccharides contribute substantially to the viscosity of the syrup and thus the syrup cannot be used to effectively replace higher DE syrups, even though it does have a reduced sugar (DP1+2) content.

TABLE 4

| Sample | Dextrose | DP2 | DP3 | DP4 | DP5 | DP6 | DP7 | DP8 | DP9 | DP10 | DP11 | DP12 | DP13+ |
|---|---|---|---|---|---|---|---|---|---|---|---|---|---|
| Veretase ® Liq | 0.51 | 4.12 | 4.76 | 3.66 | 3.15 | 5.81 | 8.84 | 6.58 | 6.10 | 4.73 | 0.00 | 0.00 | 51.73 |
| t = 0 | 0.94 | 6.29 | 7.27 | 8.92 | 4.50 | 7.58 | 10.00 | 7.13 | 5.71 | 5.34 | 0.00 | 0.00 | 36.30 |
| t = 0.5 hr | 1.99 | 9.25 | 11.13 | 27.26 | 4.27 | 5.57 | 5.60 | 7.59 | 3.93 | 3.89 | 0.00 | 0.00 | 19.45 |
| t = 1 hr | 2.64 | 10.85 | 12.52 | 34.42 | 3.89 | 4.89 | 4.80 | 6.70 | 3.39 | 3.49 | 2.77 | 0.00 | 9.55 |
| t = 1.5 hr | 3.05 | 11.89 | 13.23 | 37.99 | 3.65 | 4.50 | 4.35 | 5.78 | 3.19 | 2.90 | 9.37 | 0.00 | 0.00 |
| t = 2 hr | 3.33 | 12.58 | 13.55 | 39.76 | 3.52 | 4.30 | 4.12 | 5.20 | 3.11 | 2.64 | 7.80 | 0.00 | 0.00 |
| t = 2.5 hr | 3.62 | 13.31 | 13.84 | 41.04 | 3.42 | 4.11 | 4.01 | 4.68 | 3.02 | 2.18 | 6.65 | 0.00 | 0.00 |
| t = 3 hr | 3.95 | 14.08 | 14.02 | 41.66 | 3.42 | 4.05 | 3.98 | 4.28 | 2.85 | 2.08 | 5.51 | 0.00 | 0.00 |

What is claimed is:

1. A method of making a reduced sugar, lower viscosity syrup for food, beverage, animal feed, animal health and nutrition, pharmaceutical, and cosmetic compositions, comprising:
    (a) jet cooking a slurry comprising a starch or a starchy material, an alpha amylase enzyme and an aqueous medium at a first temperature of 100° C. to 115° C., then transferring said slurry to a vessel such that said slurry is resident in a tail line for a period of time of 5 to 8 minutes;
    (b) maintaining said slurry in said vessel at a second temperature of 80° C. to 95° C. for a time effective for said alpha amylase to hydrolyze said starch or said starchy material to provide a reaction product comprising a saccharide distribution having a DP1+DP2 content of 10% to 25%, a DP3-11 content of 70% to 90%, and a DP11+ content of 0% to 15%, wherein the pH of said slurry is not adjusted or changed after step (a) before proceeding with step (b); and
    (c) subjecting said reaction product to one or more purification or processing steps to provide said reduced sugar, lower viscosity syrup, wherein said syrup has a reduced sugar content as compared to a 63 DE corn syrup and a viscosity of less than 1500 poise at 20° C. when said syrup has a dry solids content of 80%;
    wherein said alpha amylase is a polypeptide encoded by a nucleotide sequence having at least 95% sequence identity to the nucleotide sequence of SEQ ID NO: 1, and wherein the only type of enzyme used in said method is said alpha amylase enzyme.

2. The method of claim 1, wherein step (c) comprises filtering said reaction product.

3. The method of claim 1, wherein step (c) comprises contacting said reaction product with activated carbon.

4. The method of claim 1, wherein step (c) comprises contacting said reaction product with an ion exchange resin.

5. The method of claim 1, wherein step (c) comprises removing water from said reaction product to achieve a dry solids content of 65% to 85%.

6. The method of claim 1, wherein step (c) comprises filtering said reaction product, contacting said reaction product with activated carbon and an ion exchange resin, and removing water from said reaction product to achieve a dry solids content of 65% to 85%.

7. The method of claim 1, wherein step (c) comprises subjecting said reaction product to ultrafiltration using a membrane.

8. The method of claim 1, further comprising combining said syrup with at least one high intensity sweetener.

9. The method of claim 1, wherein said starch or said starchy material is not contacted with acid.

10. The method of claim 1, wherein said aqueous medium initially has a pH of 5 to 7.

11. The method of claim 1, wherein an amount of said alpha amylase enzyme is from 0.01 to 0.2 weight % of the amount of said starch or said starchy material.

12. The method of claim 1, wherein said starch is a corn starch or said starchy material is from corn.

13. The method of claim 1, wherein said DP11+ content is from 0-5%.

* * * * *

SEQUENCE LISTING

<160> NUMBER OF SEQ ID NOS: 3

<210> SEQ ID NO 1
<211> LENGTH: 1311
<212> TYPE: DNA
<213> ORGANISM: Artificial Sequence
<220> FEATURE:
<223> OTHER INFORMATION: Synthetic

<400> SEQUENCE: 1

```
atggccaagt actccgagct ggaaaagggc ggggtcataa tgcaggcgtt ctactgggac      60
gtgccttcag gaggaatatg gtgggacaca atacggcaga agataccgga gtggtacgat     120
gccggaatct ccgcaatatg gattcccccg gcgagcaagg gcatgggcgg cgcctattcg     180
atgggctacg acccctacga cttctttgac ctcggtgagt acgaccagaa gggaacggta     240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360
aaccccttcg tgaacgacta tacctggacc gacttctcaa aggtcgcgtc gggtaaatac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg ggtcgtcaag gactggctga actggtgggg aggctgggcg     660
gttggagagt actgggacac caacgtcgac gctgttctca actgggcata ctcgagcggt     720
gccaaggtct ttgacttcgc cctctactac aagatggatg aggcctttga caacaaaaac     780
attccagcgc tcgtctctgc ccttcagaac ggccagactg ttgtctcccg cgacccgttc     840
aaggccgtaa cctttgtagc aaaccacgac accgataaat tctggaacaa gtatccagcc     900
tacgcgttca tcctcaccta cgagggccag ccgacaatat tctaccgcga ctacgaggag     960
tggctcaaca aggataagct caagaacctc atctggatac atgagaacct cgccggagga    1020
agcaccgaca tagtctacta cgataacgat gaactcatct tcgtcaggaa cggctacggg    1080
gacaagccgg ggcttataac ctacatcaac ctaggctcga gcaaggccgg aagtgggtt     1140 tatgtgccga agttcgcggg cgcgtgcatc cacgagtata ctggtaacct cggaggctgg    1200
gtagacaagt acgtctactc aagcggctgg gtctatctcg aagctccagc ttacgaccct    1260
gccaacgggc agtatggcta ctccgtgtgg agctactgcg gggtgggctg a             1311
```

<210> SEQ ID NO 2
<211> LENGTH: 427
<212> TYPE: PRT
<213> ORGANISM: Artificial Sequence
<220> FEATURE:
<223> OTHER INFORMATION: Synthetic

<400> SEQUENCE: 2

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
                100                 105                 110

Val Val Pro Asn His Met Asn Arg Gly Tyr Pro Asp Lys Glu Ile Asn
            115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
                180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Gly Pro
210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
                260                 265                 270

Gly Leu Asn Gly Asn Pro Asp Pro Arg Trp Arg Glu Val Ala Val Thr
                275                 280                 285

Phe Val Asp Asn His Asp Thr Gly Tyr Ser Pro Gly Gln Asn Gly Gly
            290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Trp Tyr Trp Ser His Met Tyr
                325                 330                 335

Asp Trp Gly Tyr Gly Asp Phe Ile Arg Gln Leu Ile Gln Val Arg Arg
                340                 345                 350

Thr Ala Gly Val Arg Ala Asp Ser Ala Ile Ser Phe His Ser Gly Tyr
            355                 360                 365

Ser Gly Leu Val Ala Thr Val Ser Gly Ser Gln Gln Thr Leu Trp Ala
                370                 375                 380

Leu Asn Ser Asp Leu Ala Asn Pro Gly Gln Val Ala Ser Gly Ser Phe
385                 390                 395                 400

Ser Glu Ala Val Asn Ala Ser Asn Gly Gln Val Arg Val Trp Arg Ser
```

```
                    405                 410                 415
Gly Ser Gly Asp Gly Gly Asn Asp Gly Gly
            420                 425

<210> SEQ ID NO 3
<211> LENGTH: 436
<212> TYPE: PRT
<213> ORGANISM: Artificial Sequence
<220> FEATURE:
<223> OTHER INFORMATION: Synthetic

<400> SEQUENCE: 3

Met Ala Lys Tyr Ser Glu Leu Glu Lys Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Glu Asn
                325                 330                 335

Leu Ala Gly Gly Ser Thr Asp Ile Val Tyr Tyr Asp Asn Asp Glu Leu
```

```
                340                 345                 350
Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
        370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
        435
```